US00PP12363P2

(12) United States Plant Patent
Utecht

(10) Patent No.: US PP12,363 P2
(45) Date of Patent: Jan. 22, 2002

(54) GERANIUM PLANT NAMED 'FISOM'

(75) Inventor: Angelika Utecht, Montabaur (DE)

(73) Assignee: FlorFis AG, Binningen (CH)

( * ) Notice: Subject to any disclaimer, the term of this patent is extended or adjusted under 35 U.S.C. 154(b) by 0 days.

(21) Appl. No.: 09/772,846

(22) Filed: Jan. 31, 2001

(51) Int. Cl.[7] ..... A01H 5/00
(52) U.S. Cl. ..... Plt./329
(58) Field of Search ..... Plt./329, 325

(56) References Cited

PUBLICATIONS

GTITM UPOVROM Citation for 'Fisom' as per QZ PBR 991467; Oct. 20, 1999.*
Fischer–Schmüllung Plant Alliance Catalogue featuring 'FISOM' on p. 11, Germany, 2001.
German Plant Application and Denomination—'FISOM' (Dec. 15, 1998).
Official Gazette of the Community Plant Variety Office, 'FISOM', European Community Application (Dec. 15, 1999).
Canadian Application, Denomination, Plant Varieties Journal No. 38, Jan. 2001, Canada. pp. 49–50.

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisom' as described and illustrated, and particularly characterized by the combined features of brilliant purple-pink flowers with dark-red eyes, relatively large, round umbels, medium-green, slightly zoned foliage, medium-sized plant habit, and mid season spring flowering response.

1 Drawing Sheet

BACKGROUND OF THE INVENTION

The present invention comprises a new and distinct cultivar of geranium, botanically known as *Pelargonium zonale*, and hereinafter referred to by the cultivar name 'Fisom'.

'Fisom' is a product of a planned breeding program which had the objective of creating new geranium varieties with purple flower color, in combination with intense green foliage, and medium sized plant habit. 'Fisom' originated from a hybridization made by the inventor Angelika Utecht in a controlled breeding program in Galdar, Gran Canaria, Spain, in 1995.

The female parent was the patented variety 'Fisdino', U.S. Plant Pat. No. 8,761, having purple-pink semi-double flowers with distinct eyes, medium green, zoned foliage, and moderately vigorous growth habit. The male parent of 'Fisom' was a hybrid seedling, no. 998-9 (unpatented), characterized by dark-pink flowers with white macules at the bases of upper petals, and medium-green, zoned foliage.

'Fisom' was selected as one flowering plant within the progeny of the stated cross by Angelika Utecht in 1996 in a controlled environment in Galdar, Gran Canaria, Spain. The first act of asexual reproduction of 'Fisom' was accomplished when vegetative cuttings were taken from the initial selection in the fall of 1996 in a controlled environment in Galdar, Gran Canaria, Spain, by, or under the supervision of, Angelika Utecht.

Horticultural examination of plants grown from cuttings of the plant initiated in May 1998 in Hillscheid, Federal Republic of Germany, and continuing thereafter, has demonstrated that the combination of characteristics as herein disclosed for 'Fisom' are firmly fixed and are retained through successive generations of asexual reproduction.

'Fisom' has not been observed under all possible environmental conditions. The phenotype may vary significantly with variations in environment such as temperature, light intensity and day length.

BRIEF DESCRIPTION OF THE INVENTION

The following observations, measurements, and comparisons describe plants grown in Hillscheid, Germany, and in Langley, British Columbia, Canada, under greenhouse conditions which approximate those generally used in commercial practice.

The following traits have been repeatedly observed and are determined to be basic characteristics of 'Fisom' in combination distinguish this geranium as a new and distinct cultivar:

1. Brilliant purple-pink colored flowers with red and white markings;

2. Relatively large, round inflorescences;

3. Medium-green foliage with slight zonation;

4. Medium-sized plant habit, and good branching characteristics; and

5. Mid-season spring flowering response.

Of the many commercial cultivars known to the present inventor, the most similar in comparison to 'Fisom' is the parental variety 'Fisdino'.

In comparison to 'Fisdino', 'Fisom' has a slightly more bluish main flower color and partly different kind of markings. While 'Fisdino' has salmon-red coloring at the bases of the upper petals, 'Fisom' has small white bases. Furthermore, 'Fisom' branches more easily, and develops a more uniform and round plant habit, and is somewhat less tall than 'Fisdino'.

BRIEF DESCRIPTION OF THE DRAWING

The accompanying photographic drawing shows typical flower and foliage characteristics of 'Fisom' with colors being as true as possible with an illustration of this type. The photograph is a side view of a flowering potted plant. The measurements were taken in Langley, British Columbia, Canada, on Jul. 20, 2000, 15 weeks after planting of rooted cuttings into 6 inch pots. The plants had not been pinched.

In the following description, color references are made to The Royal Horticultural Society Colour Chart (R.H.S.). The color values were determined indoors from plants developed in a green-house in May 2000, in Hillscheid, Germany.

Classification:

*Botanical.*—A hybrid of the species *Pelargonium zonale* L'Hérit.

*Commercial.*—Zonal geranium, cv. 'Fisom'.

Inflorescence:

*Umbel.*—Shape: Semi-spherical to nearly spherical. Average diameter: 116 mm. Average depth: 70 mm. Peduncle length: 178 mm. Peduncle color: Grass-green, RHS 143 A. Pedicel length: 27 mm. Pedicel color: Light green, RHS 143 C, at the base, upper part light red RHS 179 C to reddish-browh RHS 178 A. Number of flowers per umbel: Approximately 30. Lastingness of umbel: Approximately 16–18 days at 18° C.

*Corolla.*—Average diameter: 44 mm. Form: Semi-double. Shape: Nearly round, but with a narrow gap between upper and lower petals. Number of petals: 6–9. Petal size: Upper petals (2): 24–26 mm in length, 15–17 mm in diameter; lower petals: 22–24 mm in length, 19–20 mm in diameter. Inner petals are approximately the same size as lower petals. Petal shape: Oblong to nearly obovate, upper end is rounded with attenuate base, margin entire. Color (general tonality from a distance of three meters): Intense purple-pink with deep red eyes. Color of upper petals: Varies between RHS 74 B and RHS 67 B. Markings of upper petals: Relatively large, red eyes, varies between RHS 57 A and 66 A, and small white bases RHS 155 D. Color of lower petals: Varies between RHS 74 B and RHS 67 B. Markings of lower petals: Smaller red eyes, RHS 66 A. Color of lower surface of petals: RHS 74 C or lighter, fading toward bluish-pink RHS 68 B, with whitish-pink stripes, RHS 65 D, between the veins at the base. Number of petaloids: 1–2. Petaloid color: Upper surface purplish-pink RHS 67 B, lower surface RHS 74 C. Color of sepals: Outer surface green, between RHS 143 A and RHS 143 B, base with reddish-brown spot RHS 179 A; inner surface light green RHS 147 C, with reddish base closest to RHS 47 A. Number of sepals: 5. Sepal size: 10–12 mm in length, 4 mm in diameter for the upper sepal; 2–3 mm in diameter for the other sepals. Sepal shape: Linear to lanceolate, acute tip, base truncate, margin entire.

*Bud*: (*just prior to petals unfolding*).—Shape: Narrow elliptical to elliptical. Sepal Color (lower part): Light green, varying between RHS 143 B and RHS 143 C. Petal Color (upper part): Purple-pink, varying between RHS 74B and RHS 67 B. Length: 18 mm. Width: 8–9 mm.

*Reproductive organs.*—Androecium: 7 fertile anthers, white filaments, orange pollen, RHS 33 A, plentiful pollen production. Gynoecium: 5–6-lobed, dark-red stigma, RHS 46 A, and red style; one pistil per flower. Fertility/seed set: Occasionally a few seeds are developed; oblong shape, 4–5 mm long, brown, RHS 177B. Fruit: Oblong shape, approximately 6 mm long, rostrum about 40 mm long when ripe, green, RHS 143 A to RHS 143 B.

*Spring flowering response period.*—In Hillscheid, Germany, in 2000, plants had on average 0.8 flowers opened 8 weeks after planting of rooted cuttings.

*Outdoor flower production.*—Average number of flowers, the flower count in 2000, in Hillscheid, Germany, indicated about 2–3 inflorescences per plant in mid-May.

*Durability.*—Good stability of flower color, not quite resistant against being scorched/burnt by the sun, fair rain resistance.

*Lastingness of individual bloom.*—Approximately 8 days at 18° C.

*Fragrance.*—None.

Plant:

*Foliage.*—Shape: Kidney-shaped. Apex: Rounded. Base: Open to wide open, cordate. Margin: Bicrenated; wavy with weak expression of lobes. Size of leaf: 92 mm wide, 55–60 mm long. Color of upper surface: Medium green, approximately RHS 137 C. Color of lower surface: RHS 137 D. Color of zonation: Weak, dark-green to brown, RHS 147 A to RHS 166 A. Petiole: 50–60 mm in length, 3–3.5 mm in diameter, RHS 137D.

*General appearance and form.*—Stem color: Green, RHS 143 A. Internode length: 5–15 mm. Branching pattern: 4.6 branches. Plant size: 21.5 cm in height from the soil to the surface of the foliage; 35 cm wide.

Disease/pest resistance/susceptibility: None observed to date.

I claim:

1. A new and distinct cultivar of geranium plant named 'Fisom' as described and illustrated.

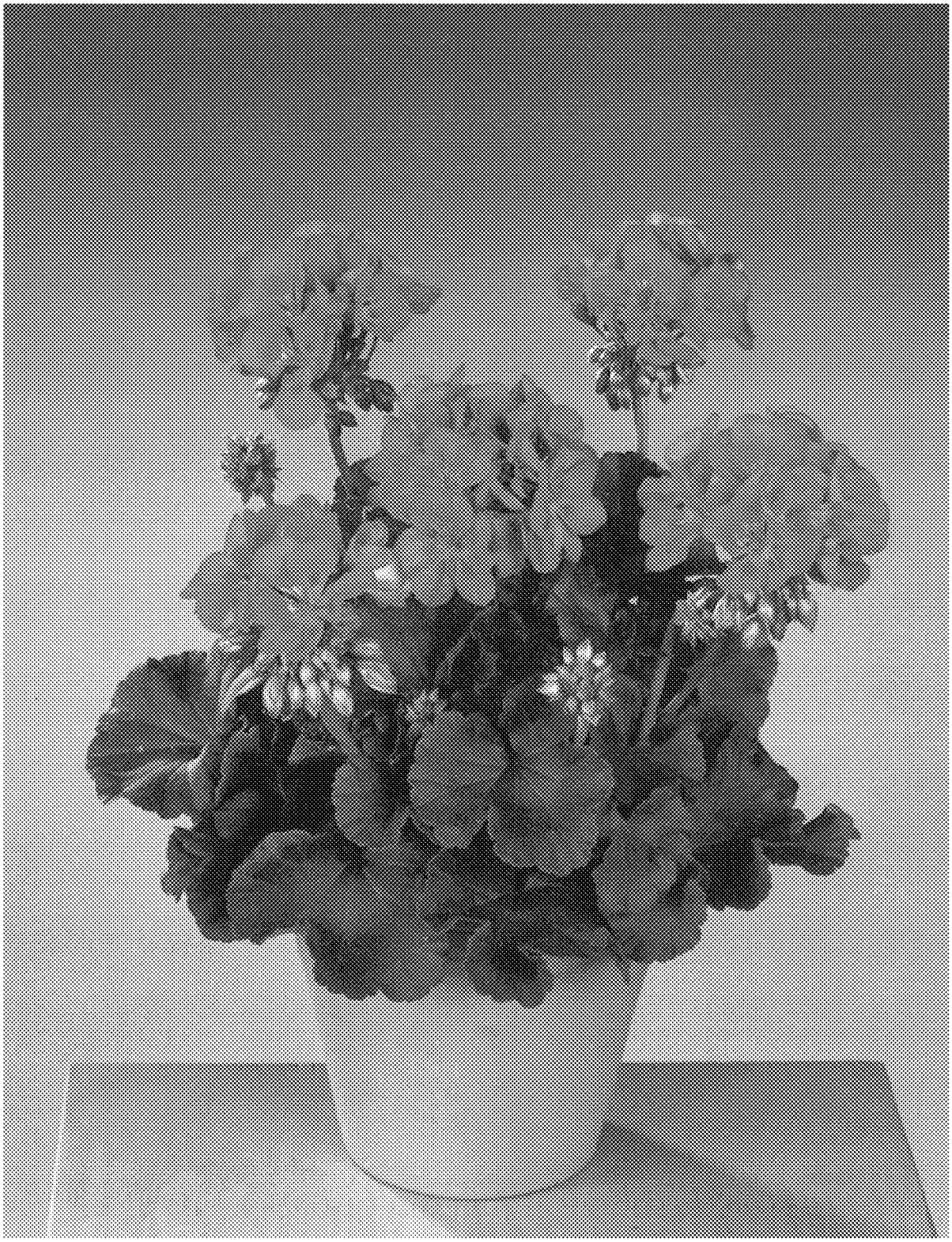

* * * * *